United States Patent [19]

Hoitink

[11] Patent Number: 4,642,131
[45] Date of Patent: Feb. 10, 1987

[54] PRODUCTION OF DISEASE SUPPRESSIVE COMPOST AND MICROORGANISM CULTURE FOR USE THEREIN

[75] Inventor: Harry A. J. Hoitink, Wooster, Ohio

[73] Assignee: The Ohio State University, Columbus, Ohio

[21] Appl. No.: 757,389

[22] Filed: Jul. 22, 1985

Related U.S. Application Data

[63] Continuation-in-part of Ser. No. 519,691, Aug. 2, 1983, abandoned.

[51] Int. Cl.$^4$ ............................................. C05F 11/08
[52] U.S. Cl. ............................................. 71/6; 71/9; 71/12; 71/23; 71/24; 435/253; 435/254; 435/850; 435/879; 435/945
[58] Field of Search ............... 435/253, 254, 850, 874, 435/945; 71/5, 6, 9, 12, 23, 24

[56] References Cited

U.S. PATENT DOCUMENTS 2,034,678  3/1936  Knaust et al. .............................. 71/5
4,214,985  7/1980  Booenrader et al. ................... 71/12

OTHER PUBLICATIONS

Wolf et al, The Fungi, 1947, pp. 280-287.

Primary Examiner—Ferris H. Lander
Attorney, Agent, or Firm—Sidney W. Millard

[57] ABSTRACT

Compost is rendered suppressive to plant pathogens, such as *Rhizoctonia solani, Pythium ultimum* and *Fusarium*, and/or diseases caused thereby by adding to the compost, desirably after peak heating has been achieved but before substantial recolonization of the compost by mesophilic microorganisms has occurred, one or more microorganisms antagonistic to the plant pathogen. Desirably the inoculated antagonistic microoganisms comprise *Trichoderma hamatum* species A.T.C.C. No. 20765 or 20764, together with a *Pseudomonas maltophilia* bacterium species A.T.C.C. No. 53199 or a *Flavobacterium* species, A.T.C.C. No. 53198.

18 Claims, 6 Drawing Figures

PRODUCTION OF DISEASE SUPPRESSIVE COMPOST AND MICROORGANISM CULTURE FOR USE THEREIN

The U.S. Government has certain rights to this invention pursuant to Environmental Protection Agency Grant No. CR-810581-01-0.

This application is a continuation-in-part of my copending application Ser. No. 519,691 filed Aug. 2, 1983 and now abandoned.

BACKGROUND OF THE INVENTION

This invention relates to methods for the production of disease suppressive compost, and microorganism cultures for use in such methods. More particularly, this invention relates to methods for the production of disease suppressive compost in which one or more microorganisms antagonistic to plant pathogens are added to the compost, the timing of the addition of the microoranisms to the compost preferably being carefully controlled to produce the greatest suppression of the pathogens.

A variety of microorganisms, especially members of the genera Trichoderma and Pseudomonas, are antagonists to plant pathogens such as *Rhizoctonia solani*, *Pythium ultimum* and others. Furthermore, it is known that suppression of such pathogens in commercial crops such as radishes may be achieved by using on such crops a compost containing relatively high concentrations of the antagonistic microorganisms. However, hitherto it has not been possible to produce, in a reproducible manner, composts containing sufficient numbers of the antagonistic microorganisms. Composts produced in windrows are typically recolonized, after peak heating, by large numbers of different microorganisms and, although some of these microorganisms are of antagonistic varieties, hitherto there has been no way of ensuring that the antagonistic microoganisms do achieve sufficient population densities to render the resulting compost suppressive to the plant pathogens.

The need for some method to produce sufficient populations of antagonistic microorganisms in compost is exacerbated by recent changes in commercial manufacture of compost. Until recently, most compost has been prepared in windrows or aerated piles exposed to weather. Recently, however, controlled processes using aerated silos or aerated tanks have been developed; in such processes, the material to be composted is placed in a substantially enclosed container through which air is forced in a controllable manner. Such processes allow better control over composting conditions and thus produce a more uniform product. Unfortunately, composts produced under such controlled conditions are normally recolonized after peak heating by a less diverse microflora than compost produced in windrows, so that compost produced under such controlled conditions is less likely to be suppressive to plant pathogens.

Furthermore, with the increased attention being paid in recent years to reducing pollution of the environment, and more specifically pollution of surface waters, a large number of additional and/or refurbished sewage plants have been constructed. Such plants produce large quantities of sludge which must be disposed of, and the most convenient way to dispose of such sludge is composting followed by use of the composted sludge on agricultural land. However, the techniques used for composting sewage sludge in modern plants are not conducive to colonization of the sludge by antagonistic microorganisms which will render it suppressive to plant pathogens such as Rhizoctonia and Pythium. Consequently, if such composted sewage sludge is to be rendered suppressive to such pathogens, as is highly desirable where the composted sewage sludge is to be used for agricultural purposes, artifical inoculation of the composted sewage sludge with antagonistic microoganisms is necessary.

Finally, in view of the significant losses caused to various commercial crops by Rhizoctonia and Pythium, it is highly desirable that compost should be suppressive to both these pathogens, and prior art methods do not yield composts which are reliably suppressive to both pathogens.

It will thus be seen that there is a need for a method of reproducibly producing a compost suppressive to plant pathogens, and specifically a need for a method of reproducibly producing a compost suppressive to both Rhizoctonia and Pythium. Furthermore, the method to be used for producing such suppressive compost should be usable in controlled composting processes, particularly those now used for composting sewage sludge, as well as in Windrow or aerated pile composting processes. This invention seeks to provide methods for producing such suppressive composts, and a microorganism culture for use in such methods.

SUMMARY OF THE INVENTION

As will be explained in more detail below, there have been isolated from soils two fungi and two bacteria which, when used in proper combinations in the inoculation of compost, are effective in rendering the compost suppressive to diseases caused by both *Rhizoctonia solani* and *Pythium ultimum*.

Accordingly, in one aspect this invention provides a biologically pure culture for inducing suppression of plant pathogens and/or diseases caused thereby in a compost, this culture consisting essentially of at least one Trichoderma fungus selected from the group consisting of *Trichoderma hamatum* isolate 382, A.T.C.C. No. 20765 and *T. hamatum* isolate 559, A.T.C.C. No. 20764, and at least one baterium selected from the group consisting *Pseudomonas maltophilia* sp. isolate 76, A.T.C.C. No. 53199 and Flavobaterium sp. isolate 299, A.T.C.C. No. 53198.

In another aspect, this invention provides a method for producing a compost which is suppressive to at least *Rhizoctonia solani* and *Pythium ultimum* and/or diseases caused thereby, which method comprises inoculating into said compost at least one Trichoderma fungus selected from the group consisting of *Trichoderma hamatum* isolate 382, A.T.C.C. No. 20765 and *T. hamatum* isolate 559, A.T.C.C. No. 20764, and at least one baterium selected from the group consisting of *Pseudomonas maltophilia* sp. isolate 76, A.T.C.C. No. 53199 and Flavobacterium sp. isolate 299, A.T.C.C. No. 53198.

This invention also provides a biologically pure culture consisting essentially of any one or more of the following microoganisms:
*Trichoderma hamatum* isolate 382, A.T.C.C. No. 20765;
*Trichoderma hamatum* isolate 559, A.T.C.C. No. 20764;
*Pseudomonas maltophilia* sp. isolate 76, A.T.C.C. No. 53199; and
Flavobacterium sp. isolate 299, A.T.C.C. No. 53198

Furthermore, although it might at first appear that all that is necessary to produce a compost suppressive to diseases caused by plant pathogens is to introduce into the material being composted a sufficient quantity of an appropriate antagonistic microoganism, it has been found that this is not necessarily the case, and that unless the antagonistic microoganism is added at a particular time during the composting process, the population of the antagonistic microorganism or microorganisms in the compost may not increase to the levels necessary to make the entire compost suppressive. In particular, it has been found that the best results are obtained by adding the antagonistic microorganism or microoganisms to the material being composted after peak heating has been achieved but before substantial recolonization of the compost by mesophilic microorganisms has occurred.

Accordingly, this invention provides a method for producing a compost which is suppressive to a plant pathogen, and/or a disease caused thereby, this method comprising inoculating into the compost, after peak heating has been achieved but before substantial recolonization of the compost by mesophilic microorganisms has occurred, at least one microoganism suppressive to the plant disease.

As indicated by the A.T.C.C. reference numbers quoted above, the four preferred microoganisms for use in the cultures and methods of the present invention have all been deposited in the American Type Culture Collection, 12301 Parklawn Dr., Rockville, Md. 20852, under the deposit numbers quoted above. These deposits have been made under conditions that specify:

(a) access to the culture will be available during pendency of this patent application (or any continuation, division, or continuation-in-part thereof) to one determined by the Commissioner of Patents and Trademarks to be entitled thereto under U.S. Code Title 35, Section 122 and Code of Federal Regulations, Title 37, Section 1.14; and (b) that all restrictions on the availability to the public of the deposited culture will be irrevocably removed on the granting of a patent on any of the aforementioned applications.

DETAILED DESCRIPTION OF THE INVENTION

Figure 1:
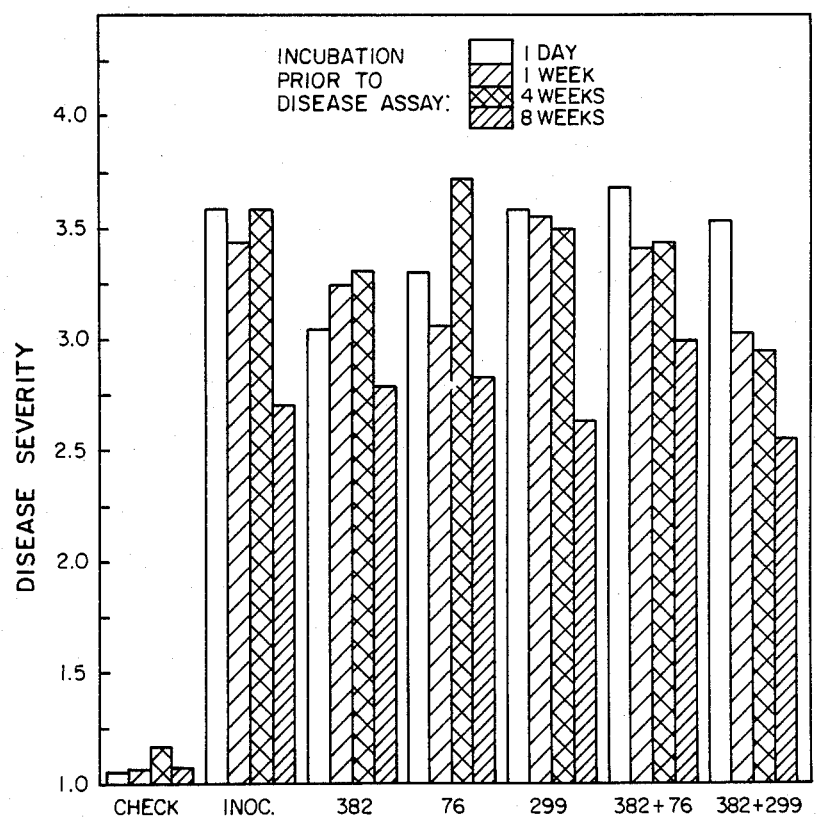
FIG. 1 is a graph showing the effect of antagonistic microoganisms and incubation time on the severity of Rhizoctonia damping-off of radish in a peat medium.

As already mentioned, the microorganism culture of the present invention comprises *Trichoderma hamatum*, isolate 382, A.T.C.C. No. 20765, or isolate 559, A.T.C.C. No. 20764 together with either *Pseudomonas maltophilia* sp. isolate 76, A.T.C.C. No. 53199 or *Flavobacterium* sp. isolate 299, A.T.C.C. No. 53198. All four microorganisms were isolated by baiting composted sewage sludge or composted hardwood bark and isolated by routine plating techniques which will be familiar to those skilled in the art. The biological characteristics of these microorganisms are as follows:

*T. hamatum* isolate 382, A.T.C.C. No. 20765 and isolate 559, A.T.C.C. No. 20764

Isolates 382 and 559 are not morphologically different and agree closely to the species description. The following description is based on observations of cultures produced on 2% malt extract agar (difco) at 22° C. under continuous light. Colonies expand rapidly and cover plates (9 cm. diameter) in one week. Abundant sporulation is evident across the surface of the cultures in 4 to 5 days. Conidia and conidiophores are produced in discrete pustules which are initially white but rapidly (1 to 2 days) turn green; unlike many other taxa in the genus Trichoderma, the conidiophores are relatively thick and conidiophore branches are short and crowded. The terminal end of each condiophore is marked by the presence of an elongate, non-sporulating (i.e. sterile) undulating appendage. Phialides are borne on the verticilate conidiophore branches and conidia are produced in small clusters at the top of each phialide. The conidia are oval, smooth and 3.5 to 4 by 2.5 microns in size.

*Pseudomonas maltiphilia* sp. isolate 76, A.T.C.C. No. 53199

Straight or slightly curved rods, 0.5 by 1.5 microns, singly or in pairs. Gram-negative. Polar, multitrichous flaggelation. Oxidase and arginine Dihydrolase negative. Does not accumulate poly-beta-hydroxybutyrate as an intracellular carbon reserve. Colonies are yellowish, color is not due to xanthomonadins. Does not produce fluorescent pigments on King's Medium B. Does not produce diffusable pigments on King's Medium A or nutrient agar. No denitrification. Strictly aerobic. Starch hydrolysis negative. Hydrogen sulfide from cysteine positive. Grows at 41° and 25° C. Hydrolyses casein, Tween 80 and gelatin. Lecithinase positive. Utilizes glucose and maltose as sole sources of carbon and energy only with the addition of the growth factors methionine, cystine, biotin, pantothenate and cyanocobalamin. Slight growth on glucose with addition of methionine or cystine alone.

Flavobacterium sp. isolate 299, A.T.C.C. No. 52198

Rod-shaped cells with parallel sides and rounded ends, 0.5 microns wide and 1 to 3 microns long. Intracellular granules of poly-beta-hydroxybutyrate are absent. Gram-negative. Non-motile. Does not glide or spread. Aerobic, strictly respiratory. Does not grow at 41° C., grows at room temperature. Growth on nutrient agar is yellow-orange pigmented. Does not produce diffusable pigments on nutrient agar or King's Medium A. Does not fluoresce on King's Medium B. Colonies on nutrient agar (1 to 5 mm. diameter) are circular, translucent, smooth and shiny with entire edges. Oxidase positive and arginine dihydrolase negative. Acid is not produced under aerobic or anaerobic conditions from glucose. Does not utilize glucose as sole carbon and energy source without growth factors or with addition of methionine, cystine, nicotinate, glutamate, pantothenate, biotin and cyanocobalamin. Lecithinase positive. Starch, gelatin, casein and Tween 80 are hydrolyzed. Nitrate is not reduced and hydrogen sulfide is not produced from cysteine.

As will be apparent to those skilled in the art, commercial practice of the methods of the present invention will necessarily result in release of significant quantities of the inoculated microorganisms into the environment when the suppressive compost containing the microorganisms is spread on agricultural land. In view of certain plant disorders known to be associated with species of Pseudomonas, it is very doubtful whether current Environmental Protection Agency regulations will permit substantial release into the environment of the *Pseudomonas maltophilia* isolate used in the microorganism culture of the present invention, even though this isolate is not known to be associated with any pathogenic condition in plants. Accordingly, it is preferred that the bacteria used in the microorganism of the culture of the present invention be Flavobaterium sp. isolate 299, since the release of this Flavobaterium into the environment appears to pose no significant problems. Furthermore, experiments using composted hardwood bark indicate that composts amended with this Flavobacterium and with either of the *Trichoderma hamatum* isolates 382 and 559 are suppressive not only to diseases caused by *Rhizoctonia solani* and *Pythium ultimum*, but are also significantly suppressive of Fusarium wilt caused by *Fusarium oxysporum* f. sp. *conglutinans* race 2.

The term "biologically pure culture" is used herein in its conventional meaning of a culture in which substantially all of the microorganisms present are of the specified type or types i.e. one in which the microorganism population consists essentially of the specified type or types of microorganisms. The term "biologically pure culture" does not, of course, exclude the presence of very small numbers of other microoganisms which may enter the culture, nor does it exclude the presence of substantial amounts of non-microoganism material, for example nutrient media and other additives needed to enable the microoganisms to be cultured. As will be known to those skilled in the art, cultures of bacteria are normally concentrated by centrifugation during the preparation of products intended for use in inoculating compost and such concentration procedures effectively remove the nutrient in culture media which could interfere with the suppressive activity of the antagonistic bacteria in compost. Such concentration steps should be employed in preparing bacteria-containing cultures of the present invention for inoculation. However, the present invention extends to the cultures both in forms containing nutrients and in concentrated forms from which the nutrients have effectively been removed.

The fungi and bacteria used in the biologically pure cultures of the invention may be cultured in media similar to those previously used for other species of Trichoderma, Pseudomonas and Flavobacterium. Thus, for example, the Trichoderma may be cultured on acidified potato-dextrose agar, while the bacteria may be cultured on nutrient agar or King's B medium.

In the preferred method of the invention for producing suppressive compost, in which the Trichoderma and the Pseudomonas or Flavobacterium are inoculated into compost, the microorganisms may if desired be added separately. However, if it has been found more efficient to effect inoculation with a biologically pure culture containing the desired mixture of microorganisms. This method is applicable to a variety of composting materials, including composted hardwood bark, composted pine bark and composted sewage sludge. As already mentioned, the inoculation is desirably effected after peak heating has been achieved but before substantial recolonization of the compost by mesophilic microorganisms has occurred.

The quantity of microorganisms necessary to induce the required degree of suppressiveness in the resultant compost is easily determined by routine empirical tests, and may of course vary with the nature of the material being composted, the environment in which the compost is to be applied, the crop to be grown in the medium containing the compost (and in particular, susceptibility of the crop to the pathogens to which the compost is suppressive) and numerous other factors. However, in general it is preferred that at least about 100 colony forming units of each of the fungus and bacterium be added to each gram of dry weight of the compounds, and in practice addition of from about $10^5$ to about $5 \times 10^7$ cells of each of the fungus and the bacterium to each gram dry weight of the compost appears to give optimum results.

As already mentioned, this invention also provides a method for producing a compost which is suppressive to a plant pathogen, which method comprises inoculating into the compost, after peak heating has been achieved but before substantial recolonization of the compost by mesophilic microorganism has occurred, at least one microorganism suppressive to the plant pathogen. The compost to be inoculated may be, for example, a composted hardwood bark or a composted sewage sludge. Desirably, there is inoculated into the compost at least one Trichoderma fungus antagonistic to *Rhizoctonia solani* and *Pythium ultimum* and the diseases caused by these pathogens and at least one bacterium antagonistic to diseases caused by *Pythium ultimum*. Also, desirably the combination of this fungus and bacterium renders the compost suppressive to disease caused by *Fusarium oxysporum* f.sp. *conglutinans* race 2.

Microorganism other than those already mentioned may also be used even though much less effectively in this method of the invention. Thus, to produce compost suppressive of *Rhizoctonia solani*, the compost may be inoculated with fungi of the genera Trichoderma, Gliocladium, Penicillium, Mortierella, Paecilomyces, Geomyces, and Ophiostoma. Particularly preferred species of such fungi include *Trichoderma harzianum, T. viride, T. koningii, T. hamatum, Geomyces pannorum* var. *pannorum, G. pannorum* var. *asperulatus, Pennicillium montanense, P. griseofulvum, P. fellutinum, P. purpurogenum, P. ochrochloron, Mortierella vinacea, M. isabellina, M. zychae, M. alpina, Paecilomyces inflatus, Ophiostoma stenocera* and *Gliocladium virens*.

When the material being composted is hardwood bark, the microorganism is desirably added to the composted material after it has been composted at least for about 23 weeks, although those skilled in the art will appreciate that the exact length of composting before the microorganisms should be added will vary somewhat with the composting conditions employed, including the exact nature of the hardwood bark being composted and the temperature and other environmental conditions under which the composting is effected.

The following Examples are now given, though by way of illustration only, to show details of particularly preferred microorganism cultures and methods of the present invention.

EXAMPLE 1

Experiments were conducted to determine the ability of composted hardwood bark to suppress *Rhizoctonia solani* after the bark had been inoculated at various stages during composting with isolates of various fungi obtained from previous hardwood bark composts.

A total of 331 fungal isolates were recovered by dilution plating and baiting procedures from a peat/perlite container medium amended with composted hardwood bark. The media used were amended with bark prepared in both aerated bins and windrows, and both the bin and field (windrow) compost were used in their conducive (green) and supressive (mature) forms. Multiple cultures of the predominant fungal species isolated from the container medium were stored on potato dextrose agar slants at 4° C. for use in the experiments described below. The species of fungi isolated including the following:

Trichoderma harzianum
T. koningii
T. hamatum
T. viride
Geomyces pannorum var. pannorum
G. pannorum var. asperulatus
Penicillium montanese
P. ochrochloron
P. fellutinum
P. verrucosum var. cyclopium
P. griseolfulvum
Mortierella vinacea
M. isabellina
M alpina
M zychae
M. parvispora
M. zonata
Paecilomyces inflatus
Ophiostoma stenoceras
Gliocladium virens
Torulomyces lagena In addition, the isolates included an incompletely indentified Penicillium isolate identified as P. sp. 114, and an incompletely identified Geotrichum identified as G. sp. 36.

The ability of the resultant fungal isolates to induce suppression of *Rhizoctonia solani* in composted hardwood bark-amended container media was them tested as follows. Two types of composted hardwood bark were prepared, namely field composted hardwood bark obtained from windrows and bin composted hardwood bark obtained from a composting mass in an aerated bin. Different ages of bin compost were obtained by collecting 30 liter samples at three week intervals from a composting mass, the samples being stored at $-7°$ C. until used in experiments. Green and mature field composted hardwood bark samples were obtained from windrows in a nursery. All the composted hardwood bark types were mixed with peat and perlite in a 5:3:2 v/v ratio as described in Nelson and Hoitink, Factors affecting suppression of *Rhizoctonia solani* in container media, Phytopathology, 72:275-279 (1982). This mixture adjusts the air-filled pore space in the 10 cm. tall column used in the experiments described below to 15-20%. For certain experiments, similar media were prepared using fresh (uncomposted) hardwood bark in place of the composted hardwood bark.

Originally, it was planned to conduct tests using heated conducive (three week old) composted hardwood bark. however, preliminary experiments showed that addition of fungal isolates to this medium failed to yield consistent results, but that the necessary consistency could be substituted by using suppressive mature (44 week old) composted hardwood bark which had previously been rendered conducive by heating to 60° C. for five days. Accordingly, the heated mature composted hardwood bark medium was substituted for the proposed medium using heated conducive green hardwood bark.

For inoculation of these container media, spore suspensions of various fungal isolates were prepared by growing cultures of the isolates on potato dextrose agar at 25° C. for 21 days, then placing the resultant colonized agar in 200 ml. of sterile distilled water, stirring the resultant mixture vigorously and filtering through two layers of cheesecloth. The filtrate was then centrifuged at 10,000 g. for ten minutes and the pellet which precipitated resuspended in sterile tap water at pH 6.8. Spore concentrations were determined with a hemacytometer. The resultant aqueous spore suspension was then inoculated into the container media to produce final spore concentrations of $10^5$–$10^7$ colony forming units per gram dry weight of container medium.

An inoculum of *Rhizoctonia solani* in a chopped potato/soil mixture was prepared by a variant of the method described in Ko and Hora, A selective medium for the quantitative determination of *Rhizoctonia solani* in soil, Phytopathology, 61:707-710 (1971), and the aforementioned paper in Phytopathology, 72:275-279 (1982). To reduce variability in bioassays, the inoculum was prepared by grinding air-dired chopped potato/soil mixture in a mortar and pestle, followed by sieving through 2.0 mm and 1.0 mm sieves, the pieces remaining on the 1.0 mm sieve being used to infest the container media. This second sieve, which eliminated particles less than 1.0 mm in diameter, significantly increased the sensitivity of the assay described below. the *R. solani* inoculum was added to the spore-inoculated container medium at the rate of 0.6 g. of chopped potator/soil mixture per liter of container medium. A slow-release fertilizer was also added to the container medium, as described in the aforementioned paper in Phytopathology 72:275-279 (1982). Following addition of the *R. solani* inoculum and the fertilizer, the samples were vigorously shaken to produce a truly homogeneous mixture.

The resultant mixture was then used in a variant of the Rhizoctonia damping-off assay described in Henis et al, Integrated Control of *Rhizoctonia solani* damping-off of radish:effect of successive planting, PCNB and *Trichoderma harzianum* on pathogen and disease, Phytopathology, 68:900-907 (1978), this variant being described in the aforementioned paper in Phytopathology, 72:275-279 (1982). The medium containing the bark, fungal spores and *R. solani* inoculum and fertilizer was placed in pots containing approximately 400 ml. of the amended container medium and 32 seeds of radish (*Raphanus satius L.*, cultivar "Early Scarlet Globe", 97% germination) were placed in each pot. The seeds were covered with 1.0 cm of container medium and the pots incubated at 26° C. under a continuous illumination of 2,500 lux. The pots were saturated with tap water on alternate days and allowed to drain. After seven days, the number of healthy seedlings in each pot (five pots being used per treatment) was recorded and disease incidence (equal mean percentage of damped-off seedlings) determined.

In all experiments, container media amended with unheated suppressive bin composted hardwood bark, and similar bark which had been heated to render it conducive, were included as controls not containing any fungal isolates.

Since the incidence of disease varied considerably in both the treated container media and the controls, in most cases the results below are standardized by expressing data as a percentage of the original suppressiveness (the control containing the unheated bark) eliminated by heat (as shown by the control containing the heated bark) which could be restored by adding the potential antagonist, the spore suspension of the fungal isolate. Thus, the percentage restoration of suppression given below was calculated using the formula:

$$\% = 100(DH-DA)/(DH-D)$$

wherein:

DH is the desease incidence in the heated control;
DA is the desease incidence in the container medium amended with potential antagonist; and
D is the disease incidence in the container medium in the unheated control.

Each type of compost was prepared twice over a two year period and all experiments were repeated at least twice. Data were analyzed using simple t-tests, and analysis of variance and regression analysis where appropriate. Means were separated using LSD test and Duncan's new multiple range test. The results are shown in Table 1-4 below.

TABLE 1

Isolates From Suppressive Bin Compost

| Isolate | Mean percentage restoration of suppression |
|---|---|
| Trichoderma harzianum | 155.8 |
| Trichoderma koningii | 118.8 |
| Geomyces pannorum var. pannorum | 76.5 |
| Geomyces pannorum var. asperulatus | 55.9 |
| Penicillium ochrochloron | about 24 |
| Mortierella alpin | 20.9 |
| Mucor circinelloides | less than 20 |
| Torulomyces lagena | less than 20 |

TABLE 2

Conducive Bin Compost

| Isolate | Mean percentage restoration of suppression |
|---|---|
| Geomyces pannorum var pannorum | 48.8 |
| Paecilomyces inflatus | 48.2 |
| Ophiostoma stenoceras | 38.3 |
| Penicillium fellutinum | about 30 |
| Geomyces pannorum. var. asperulatus | about 28 |
| Penicillium ochrochloron | less than 20 |
| Botryotrichum piluliferum | less than 0 |
| Penicillium verrucosum var. cyclopium | less than −20 |
| Trichoderma harzianum | about −50 |
| Aspergillus fumigatus | about −130 |

TABLE 3

Suppressive Field Compost

| Isolate | Mean percentage restoration of suppression |
|---|---|
| Trichoderma hamatum | 81.5 |
| Penicillium montanese | 67.0 |
| Mortierella vinacea | about 32 |
| Geotrichum sp.36 | about 26 |
| Penicillium ochrochloron | about 26 |

TABLE 3-continued

Suppressive Field Compost

| Isolate | Mean percentage restoration of suppression |
|---|---|
| Penicillium griseofulvum | about 26 |
| Penicillium sp.114 | less than 20 |
| Chaetomium homopilatum | less than 20 |
| Chaetomium aureum | less than 20 |
| Mortierella parvispora | less than 10 |
| Mortierella isabellina | less than 0 |
| Trichoderma koningii | less than 0 |
| Geomyces pannorum var. pannorum | less than 0 |
| Penicillium purpurogenum | less than 0 |
| Ophiostoma stenoceras | about −20 |

TABLE 4

Conducive Field Compost

| Isolate | Mean percentage restoration of suppression |
|---|---|
| Mortierella vinacea | 52.8 |
| Penicillium ochrochloron | 50.9 |
| Mortierella isabellina | 34.2 |
| Ophiostoma stenoceras | 28.9 |
| Geomyces pannorum var. pannorum | 23.0 |
| Penicillium fellutinum | about 20 |
| Trichoderma koningii | less than 20 |
| Penicillium purpurogenum | less than 20 |
| Penicillium verrucosum var. cyclopium | less than 10 |
| Torulomyces lagena | less than 10 |

These experiments showed that a wide variety of the fungi recovered from container media amended with hardwood bark composts induced significant levels of suppression; however, in any given batch of amended medium only a small percentage of the above fungi were efficacious antagonists. Members of the genera Trichoderma, Gliocladium, Penicillium, Mortierella, Paecilomyces, Geomyces and Ophiostoma had the highest levels of antagonistic activity. The antagonistic activity of these genera is not surprising in view of reports in the literature of some of these genera as antagonists of R. solani as well as other root-infecting fungi; see for example Chet et al, Trichoderma hamatum: its hyphal interactions with Rhizoctonia solani and Pythium spp., Microbiol Ecology, 7:29-38 (1981); Domsch et al, Compendium of Soil Fungi, Vol. 1, Academic Press, New York, 1980; and Tu and Vaartaja, The Effect of the Hyperparasite (Gliocladium virens) on Rhizoctonia solani and on Rhizoctonia root rot of white beans, Can. H. Bot., 59:22-27 (1981). In general, fungal isolates from media amended with the three-week old conducive bin composts were generally not as antagonistic as isolates from media amended with suppressive bin composts (compare Tables 1 and 2); none of the isolates from the conducive media restored more than about 50% of the levels of suppression found in the unheated controls. In particular, isolates of Trichoderma harzianum and T. koningii from media amended with suppressive bin composts induced levels of suppression equal to or better than those found in media amended with the unheated suppressive composts (see Table 1). Isolates of Geomyces pannorum var. pannorum and asperulates from media amended with suppressive bin compost also induced very significant levels of suppression.

The high levels of antagonistic activity of Trichoderma hamatum isolates recovered from media amended with suppressive field compost and the similarly high level of antagonistic activity of *T. harzianum* isolated from media amended with suppresive bin compost, coupled with the high population levels of these fungi observed experimentally, suggest that these two Trichoderma fungi may be largely responsible for the suppression observed in some suppressive prior art composts.

A further series of experiments were conducted in the same manner except that the fungal isolates used were recovered from Rhizoctonia inocula (prepared in the manner described above) incubated in container media amended with suppressive or conducive composted hardwood bark. The results are shown in Tables 5 and 6 below.

TABLE 5

Media Amended with Suppressive Composted Hardwood Bark

| Isolate | Mean percentage restoration of suppression |
|---|---|
| Trichoderma hamatum | 149.9 |
| Trichoderma koningii | 98.7 |
| Gliocladium virens | 80.5 |
| Trichoderma harzianum | 43.6 |
| Mortierella zychae | 22.0 |
| Mortierella alpina | 21.6 |
| Humicola grisea | about 20 |
| No. 480 (unidentified) | less than 10 |
| Zygorrrhynchus moelleri | less than 10 |
| Mortierella parvispora | less than 10 |
| Mortierella zonata | less than 10 |
| No. 596 (unidentified) | less than 0 |
| Mortierella isabellina | less than 0 |

TABLE 6

Isolates from Inocula Incubated in Media Amended With Conducive Composted Hardwood Bark

| Isolate | Mean percentage restoration of suppression |
|---|---|
| Trichoderma harzianum | 67.4 |
| Ophiostoma stenocera | 39.4 |
| Gilmaniella humicola | about 22 |
| Aspergillus sp.735 (incompletely identified) | about 20 |
| Botryotrichum piluliferum | less than 20 |
| Epichoccum purpurascens | less than 10 |
| Rhizopus oryzae | less than 10 |
| No. 596 | less than 0 |

From the data in Tables 5 and 6, it will be seen that Trichoderma species had the highest antagonistic activity of the fungi recovered from the inocula. Although the isolates from the media amended with the suppressive composted hardwood bark induced the greatest level of suppression (compare Tables 5 and 6) it was not possible to identify a consistent relationship between the levels of antagonistic activity and source when only single isolates of individual species were compared.

The antagonistic activities of 81 isolates of four species groups of Trichoderma isolated from media amended with suppressive and conducive composted hardwood bark were compared in the same manner as previous experiments by adding the isolates at the rate of 100,000 colony forming units per gram dry weight of container medium to media amended with mature composted hardwood bark heated to 60° C. The figures given in Table 7 below are % restoration; the variations shown are the 95% confidence intervals.

TABLE 7

Restoration of Suppression by Trichoderma Species Isolated from Suppressive Conducive Container Media

| Species | No. of Isolates Tested | Source Conducive | Suppressive |
|---|---|---|---|
| T. hamatum | 25 | 50.9 ± 19.9 | 77.3 ± 26.1 |
| T. harzianum | 25 | 42.8 ± 21.3 | 63.7 ± 38.1 |
| T. koningii | 25 | 42.0 ± 15.7 | 56.5 ± 20.0 |
| T. viride | 6 | 28.1 ± 14.9 | 36.7 ± 53.8 |

Although the mean level of suppression induced by all species was apparently greater for isolates from media amended with suppressive composted hardwood bark than those amended with conducive hardwood bark, these differences were not significant at the 95% confidence level because of the high variability of isolates from a single source.

In a further series of experiments, increasing levels of a single isolate of *Trichoderma harzianum* were added to media amended with heated suppressive bin composted hardwood bark and unheated Canadian peat medium. Addition of only 100 colony forming units per gram dry weight of the composted hardwood bark amended media induced approximately 75% suppression of disease incidence, a level of suppression that was approximately equal to that induced by adding $10^8$ colony forming units per gram dry weight of the Canadian peat medium. Addition of 10,000 colony forming units per gram dry weight to the composted hardwood bark amended medium induced more than 90% suppression of disease incidence.

Experiments were also conducted to test whether the levels of suppression induced by *Trichoderma harzianum* in composted hardwood bark amended media varied with the age of the composted hardwood bark used. These experiments were conducted by adding 100 colony forming units per gram dry weight of a *T. harzianum* spore culture, produced as already described, to media amended with fresh and 3, 6 and 44 week-old composted hardwood bark. As is well known to those skilled in the art, hardwood bark composts relatively slowly, so that the three and six week old composted bark was still at the peak heating stage (which terminates at about 23 weeks) while the 44 week old bark was past the peak heating stage but not yet cooled to temperatures at which substantial recolonization by mesophilic microorganisms could be expected. Experiments were conducted using both unheated and heated mature composted hardwood bark as the amending agent and the results are shown in Table 8 below, where the columns headed 25° C. represent the unheated bark, while the columns headed 60° C. represent the bark which had previously been heated to this temperature for five days.

TABLE 8

| | Disease Incidence | | | | | | | |
|---|---|---|---|---|---|---|---|---|
| | 25° C. | | | | 60° C. | | | |
| Trichoderma added | Compost Age (weeks) | | | | Compost Age (weeks) | | | |
| | 0 | 3 | 6 | 44 | 0 | 3 | 6 | 44 |
| — | 79.2a[c] | 79.9a | 70.8ab | 45.0b | 73.4ab | 85.7a | 73.0ab | 68.5ab |

TABLE 8-continued

| Trichoderma added | Disease Incidence | | | | | | | |
|---|---|---|---|---|---|---|---|---|
| | 25° C. Compost Age (weeks) | | | | 60° C. Compost Age (weeks) | | | |
| | 0 | 3 | 6 | 44 | 0 | 3 | 6 | 44 |
| + | 73.7ab | 74.0ab | 58.1ab | 52.1ab | 53.6b | 68.2ab | 58.1b | 30.3c |

'Represents mean % damping-off after pre-incubating CHB-amended media with or without *T. harzianum*; numbers followed by the same letter are not significantly (P = 0.05) different according to Duncan's new multiple range test.

The data in Table 8 show that only media amended with the mature, 44 week old composted hardwood bark were highly suppressive. As observed in the previous experiments, addition of Trichoderma harzianum to unheated mature composted hardwood bark amended medium did not significantly decrease damping-off. However, significantly higher levels of suppression (i.e. lower disease incidence) were induced by *Trichoderma harzianum* in heated mature composted hardwood bark amended media. Addition of this fungus had no significant effect on damping-off in media amended with fresh hardwood bark or the three or six week-old batches of composted hardwood bark regardless of whether or not these media has previously been heated.

In an attempt to determine whether the differences in levels of suppression induced in *Trichoderma harzianum* with age of compost used were related to differences in population level with age of compost used, further experiments were conducted to determine the population levels of *Trichoderma harzianum* in media amended with fresh (uncomposted) hardwood bark, and three, six and 44 week-old hardwood bark. These experiments showed that the differences in levels of suppression could not be due solely to differences in fungal population since after 14 days the population levels in the fresh and six-week old bark were substantially greater than those in the 44 week old bark, with the populations in the three week old bark being the lowest; after this 14-day period, the population in the fresh hardwood bark was approximately 5 million colony forming units per gram dry weight of compost, in the six week old bark approximately 10,000 CFU/g dry weight and in the three week old bark approximately 300 CFU/g dry weight. Regression analysis of the population data and comparison of slope values showed that the populations developed at a significantly lower rate in media amended with three or 44 week old bark than in media amended with fresh or six week old bark.

From all the foregoing experiments, it was concluded that the low level of suppression in media amended with green composted hardwood bark (whether bin or field) could not be attributed to the absence of antagonistic fungi or to low levels of antagonistic activity of isolates present in those media. Tables 1-6 above show the Trichoderma, as well as other fungi capable of restoring significant levels of suppression, were present in green as well as mature composted hardwood bark. Furthermore, Trichoderma isolates from media amended with green composted hardwood bark were almost as effective inducing suppression as those isolated from media amended with mature composted hardwood bark (see Table 7 above). Furthermore, the foregoing experiments show that the low levels of disease suppression produced by conducive media are not due to limited population development of Trichoderma in such media, since the population levels obtained in media amended with fresh or six week old bark were actually greater than those obtained in the mature bark, yet suppression is significant in media amended with the mature bark (see Table 8 above). Rates of population growth were higher in the media amended with fresh or six-week old composted hardwood bark, but these media were conducive or only mildly suppressive. Therefore, disease suppression depends not only upon the presence of potential antagonistic microorganisms in composted hardwood bark amended media but also on factors which affect the activity of these organisms.

Although the activity of the antgonists were determined in media which had been heated 60° C. for five days and thus in which populations of competing microorganisms were reduced or eliminated, the results obtained with these heated media are likely to reflect those realized with antagonists in composts in the field because temperatures of around 60° C. are produced for several days after compost piles are turned; see, for example, Hoitink, Composted Hardwood Bark, A Lightweight Growth Medium with Fungicidal Properties, Plant Dis., 64:142-147 (1980).

The foregoing results also show that by careful choice of the fungal antagonists used, the level of suppression in the antagonist-fortified mature compost amended medium can be significantly higher than in unfortified medium so that controlled production of suppressive container media has been rendered feasible.

As already mentioned, the three and six-week old composted hardwood bark had not yet passed through the peak heating stage, whereas the 44-week old bark has passed through the peak heating stage but has not yet undergone complete recolonization by mesophilic microorganisms. Accordingly, the foregoing experiments show that to produce the maximum antagonistic effect, the antagonistic microorganisms should be added to the compost after peak heating has been achieved but before substantial recolonization of the compost by mesophilic microorganisms has occured.

EXAMPLE 2

This example illustrates the isolation of microorganisms useful in inducing suppression of disease caused by *Rhizoctonia solani* and *Pythium ultimum*, and processes for inducing suppression using the microorganisms isolated.

Potential antagonists were isolated from composted sewage sludge by baiting the sludge with 1-2 mm. diameter inoculum pieces of *P. ultimum* embedded in a suppressive batch of composted sewage sludge. The pieces of inoculum were sandwiched between two layers or nylon screen and stapled together to prevent losses, approximately 50 pieces of inoculum being included in each sandwich. The inoculum pieces were buried in a container medium treated with the composted sewage sludge, recovered from 0 to 40 days after burial and rinsed in sterile distilled water for 3 minutes to remove as many surface contaminants as possible. The inoculum pieces were then placed on acidified potato-dextrose agar for isolation of fungi, on yeast extract agar for isolation of actinomycetes and on nutrient agar and King's B medium for isolation of bacteria. After 48 hours incubation at room temperature on the acidified potato-dextrose agar, fungi were isolated from hyphal tips and transferred to potato-dextrose agar slants. Isolates of bacteria were streaked on nutrient agar for further purification.

The abilities of the potentially antagonistic microorganisms to induce suppression of Rhizoctonia or Pythium in various container media were tested by adding either fungal spores or bacterial cell suspensions to the test media and, on the following day, inoculating the test media with the pathogen and beginning an assay. Inocula for fungi were cultured on potato-dextrose agar plates 9 cm. in diameter for 14-21 days. Spores were collected by placing the colonized agar in 200 ml. of water and vigorously shaking the flasks. The water containing the spores was decanted, filtered through cheesecloth and the spores were then washed by centrifugation. The resultant pellets were resuspended in water and spore concentrations were determined using a hemacytometer in order to ensure a uniform inoculum density for each fungus. In these assays, $10^5$–$10^6$ spores per gram dry weight of container medium were used since previous studes had shown that this rate of inoculation was sufficent to induce suppression in media amended with mature composted hardwood bark.

Bacterial isolates were grown for 3-4 days in 50 ml. flasks of nutrient broth on a rotary shaker. The resultant cells were separated from the culture medium by centrifugation and resuspended in a phosphate buffer, pH 6.7. The bacteria were added to the container media at a concentration of $10^5$–$10^6$ cells per gram dry weight container medium.

The compost-amended container medium used in these experiments were either heated to 60° C. for 5 days in a forced air oven or prepared with compost removed from the hot center (temperature 50°–60° C.) of a compost pile. The media used were thus devoid of mesophilic microorganisms and therefore conducive. Disease severity levels obtained in media with added potential antagonists were compared with those in either heated media or media amended with center compost without added potential antagonists.

The only fungal antagonists found to suppress both Rhizoctonia and Pythium were species of *Trichoderma hamatum and T. harzianium,* especially the aforemented *T. hamatum* isolate 382. A.T.C.C. No. 20765 and isolate 559, A.T.C.C. No. 20764. One isolate of *Penicillium funiculosum* also significantly reduced Pythium disease severity. No effective actinomycete antagonists with activity against both diseases were isolated.

Only two bacterial isolates showed good activity against both diseases, namely the aforementioned Pseudomonas maltophilia isolate 76, A.T.C.C. No. 53199 and Flavobacterium isolate 299, A.T.C.C. No. 53198.

To evaluate the ability of these antagonistic microorganisms to induce suppression of Rhizoctonia and Pythium damping-off in a variety of media, further experiments were conducted in which the *T. hamatum* isolate 382, the *Pseudomonas maltophilia* isolate 76 and the Flavobacterium isolate 299 were added singly or in combination to composted sewage sludge, composted hardwood bark and peat media. The composted hardwood bark had been cured for 16 weeks to allow development of maximum activity of Trichoderma antagonists. The composted hardwood bark was removed from the center of a windrow in which the temperature at the time of collection ranged from 55°-60° C. The composted sewage sludge had been cured for 12 weeks after screening and the samples used were removed from the center of a windrow, the temperature at this central area being from 43° to 49° C. Both windrows had been turned every two weeks throughout curing.

The Trichoderma was cultured on potato-dextrose agar for two weeks. Spores were scraped off plates, suspended in water and added to the medium at an inoculation rate of $10^4$ colony forming units per gram dry weight of medium. The two bacterial isolates were cultured in nutrient broth for 96 hours at 24° C. and added to the media at an inoculation rate of $10^6$ colony forming units per gram dry weight of medium.

All the inoculated media were incubated at 24° C. in polyethylene bags at a moisture level of 30-38 weight percent. After one day, and 1, 2, 4 and 8 weeks of incubation, samples of the amended media were assayed for suppressiveness to Rhizoctonia and Pythium damping-off by growing radishes and cucumbers respectively in the media.

Figure 2:
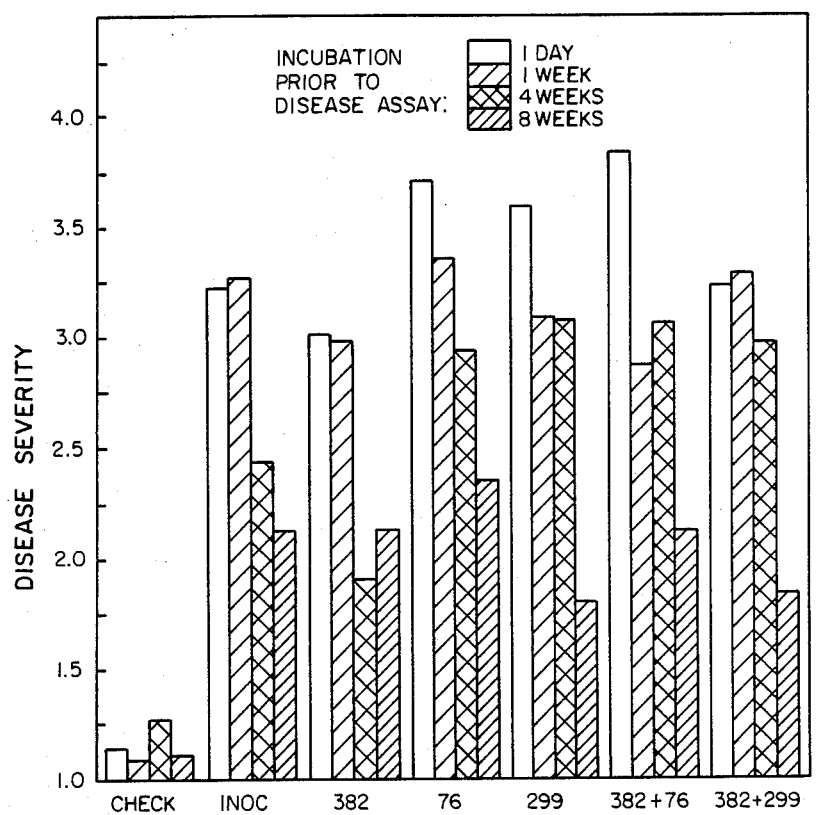
FIG. 2 is a graph similar to FIG. 1 but showing damping-off in a composted hardwood bark amended medium.
Figure 3:
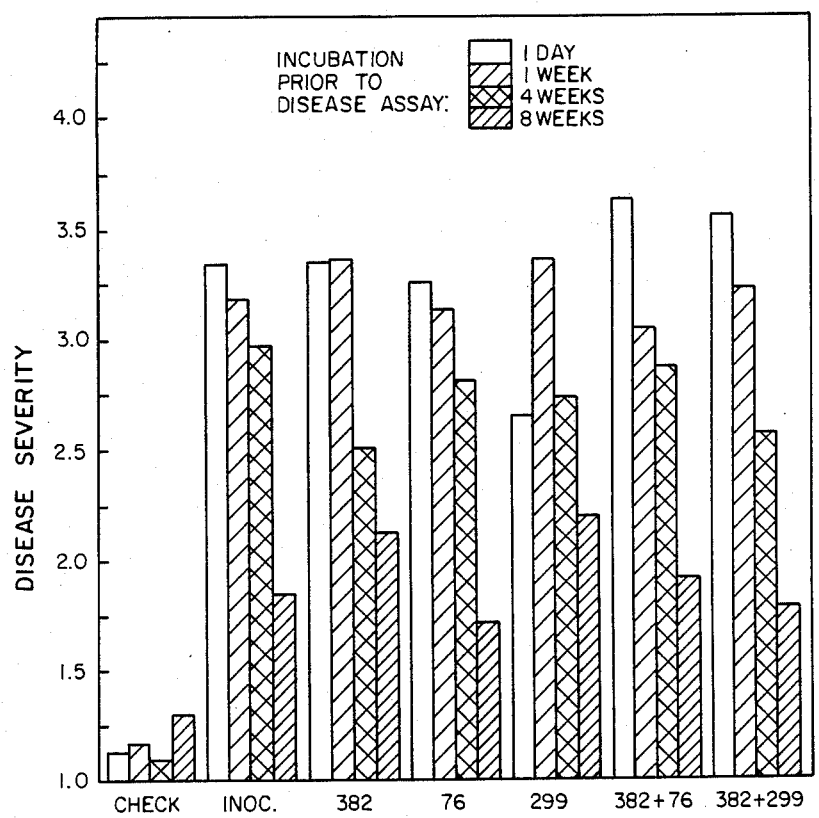
FIG. 3 is a graph similar to FIGS. 1 and 2 but showing damping-off in a composted sewage sludge amended medium.
Figure 4:
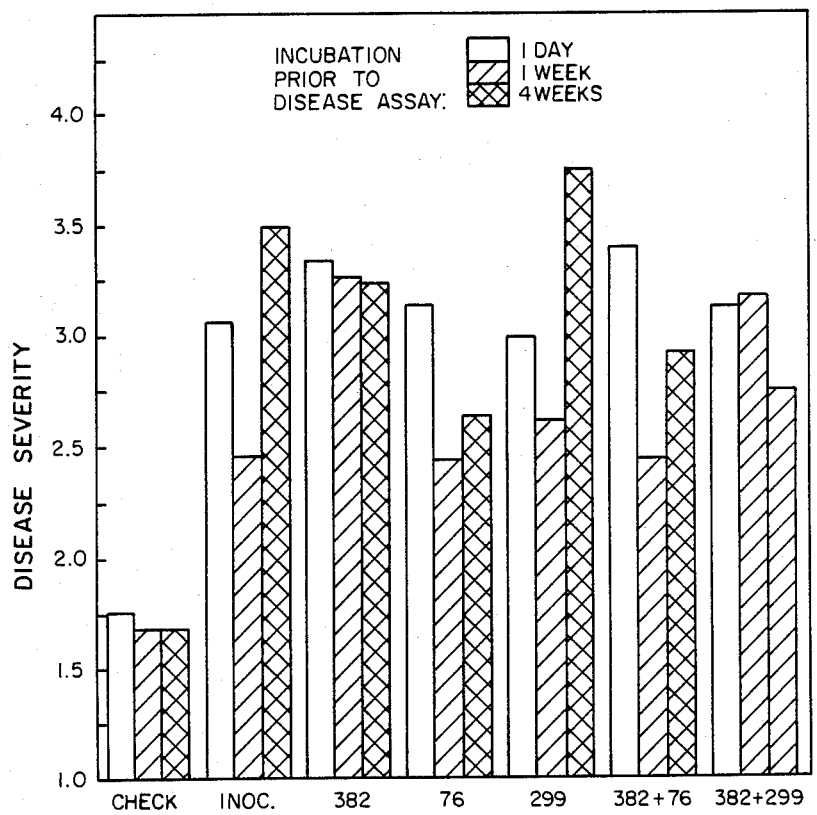
FIG. 4 is a graph showing the effect of antagonistic microoganisms and incubation time on the severity of Pythium damping-off of cucumber in a peat medium.
Figure 5:
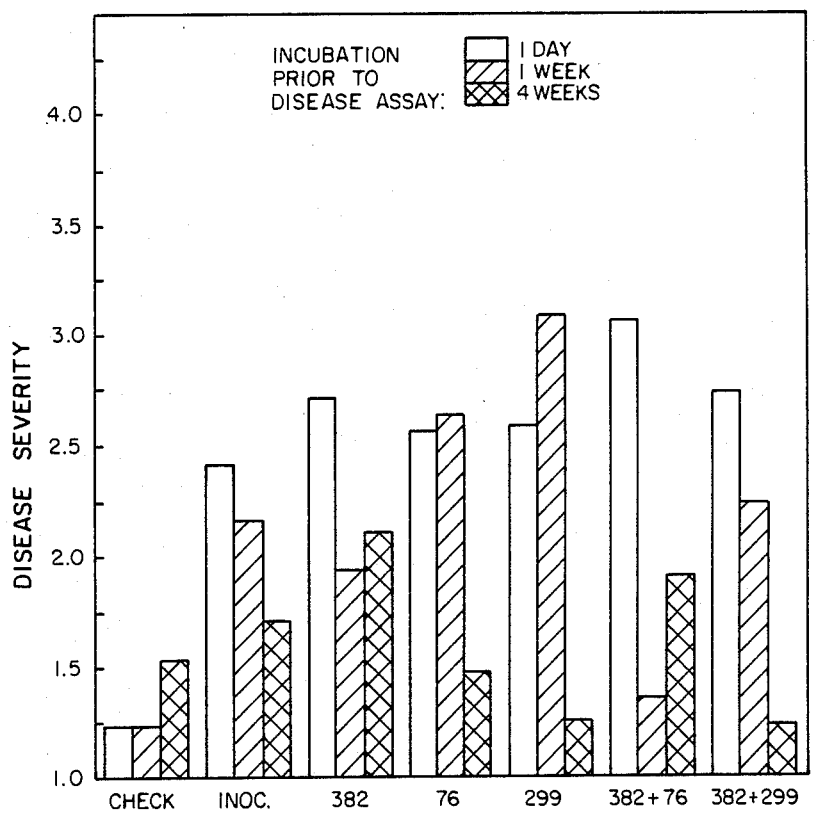
FIG. 5 is a graph similar to that of FIG. 4, but showing damping-off in a composted hardwood bark amended medium.
Figure 6:
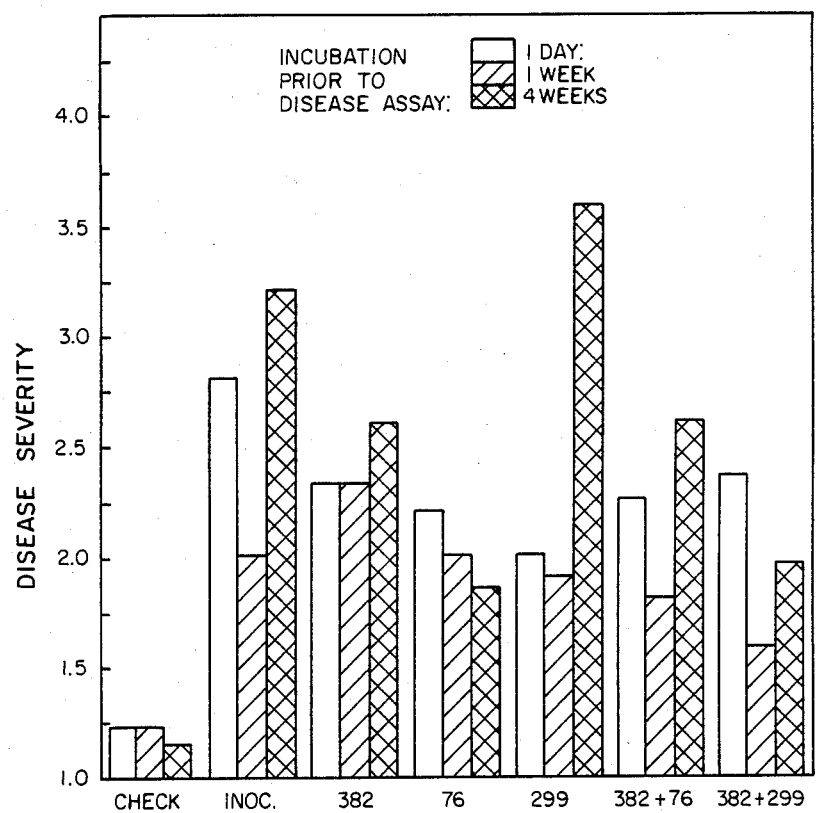
FIG. 6 is a graph similar to FIGS. 4 and 5 but showing damping-off of cucumber in a composted sewage sludge amended medium.

FIGS. 1-3 of the accompanying drawings show the results obtained with peat, composted hardwood bark and composted sewage sludge-amended media inoculated with Rhizoctonia while FIGS. 4-6 show the results obtained using the same media and Pythium inoculants. In each figure, disease severity levels are given for the uninoculated medium (designated "check"), the pathogen-inoculated medium receiving no inoculation of the antagonistic microorganism (designated "inoc.") and for the *T. hamatum* isolate 382, the *Pseudomonas maltophilia* isolate 76, the Flavobacterium isolate 299, and the combinations of isolates 382 and 76, and 383 and 299. In FIGS. 1-3, the LSD (at the 95% confidence level) is 0.36, while in FIGS. 4-6 the same parameter is 0.84.

FIGS. 1-3 showing the results for Rhizoctonia damping-off show that disease incidence was highest in the bags assayed one day after inoculation. The incidence of disease diminished with incubation time in all the media. However, disease severity levels decreased more rapidly and reached lower levels in composted hardwood bark and composted sewage sludge-amended media than in composted peak amended media. In all cases other than the uninoculated media, disease severity levels in composted peat amended media were significantly higher than in the corresponding composted hardwood bark and composted hardwood bark and composted sewage sludge amended media. Except for two exceptions noted in the following sentence, the disease severity levels observed in composted sewage sludge and composted hardwood bark amended media were not significantly different from one another. The two exceptions were the disease levels in composted hardwood bark amended media inoculated with *T. hamatum* 382, which was significantly lower than those in the corresponding composted sewage sludge amended medium and the disease levels in the composted municipal sludge inoculated with the *Pseudomonas maltophilia,* which was significantly lower than those in the corresponding composted hardwood bark amended medium The reduction in disease severity levels with incubation time in both composted hardwood bark and composted sewage sludge amended media without the addition of antagonists suggests that natural colonization of the media was sufficient to produce significant disease suppression. However, the addition of antagonists to these batches of media had a significant affect in reducing disease severity in some cases. For example, the addition of T. hamatum 382 to composted hardwood bark medium did result in significantly lower disease severity levels in comparison with the same medium which did not receive the T. hamatum. No corresponding effect of the addition of T. hamatum along was observed in composted sewage sludge amended medium.

The addition of T. hamatum 382, either alone or in conjunction with Flavobacterium 299 to peat medium significantly lowered disease severity levels but these levels still remained significantly higher than those observed in the composted hardwood bark and composted sewage sludge amended media, thus indicating that the peat medium not amended with either type of compost remained conducive.

The data presented in FIGS. 4-6 relating to suppression of damping-off caused by P. ultimum show many of the same tendencies as in the Rhizoctonia assays shown in FIGS. 1-3. In general, the levels of disease severity in the composted sewage sludge and composted hardwood bark-amended media were lower than those in the peat medium. Except for the composted sewage sludge that was not inoculated with antagonistic microorganisms, the levels of disease were significantly lower in every composted hardwood bark and every composted sewage sludge amended medium as compared with the corresponding peat medium. Furthermore, the disease severity levels in the composted hardwood bark amended media to which antagonists were added were not significantly different from one another.

As in the case of the Rhizoctonia assays, the disease severity in the Pythium assays declined with time in the composted hardwood bark amended media both with and without the addition of antagonists. Thus, natural colonization of the composted hardwood bark amended medium appeared to be sufficient to induce significant disease suppression. Disease levels in some composted hardwood bark amended media inoculated with antagonistic microorganisms were, after 8 weeks of incubation, not significantly different from their uninoculated counterparts, suggesting that the composted hardwood bark amended medium had, in this case, become naturally strongly suppressive. In contrast, in the sewage sludge amended medium, the results shown in FIGS. 4-6 indicate that natural colonization by antagonistic microorganisms either did not occur or was insufficient to result in Pythium suppression. This has also been observed in industry under commercial conditions. In the composted sewage sludge amended medium without added antagonistic microorganisms, the disease levels experienced were not significantly different from those in the corresponding peat medium. However, the addition of antagonistic microorganisms to the composted sewage sludge amended medium did significantly reduce the levels of disease severity.

Disease levels in composted sewage sludge amended media with added antagonistic microorganisms were, in all cases, significantly lower than the corresponding disease levels in peat medium. In addition, the composted sewage sludge amended medium inoculated with either Pseudomonas maltophilia 76 or the combination of T. hamatum 382 and Flavobacterium 299 displayed significantly lower disease severity levels, as compared to the same medium without the added antagonistic microorganisms.

From the foregoing results, it appears that composted hardwood bark and composted sewage sludge amended media can become suppressive to Rhizoctonia and Pythium within 4 to 8 weeks of incubation; in contrast peat media remained conducive. In the particular batch of composted hardwood bark used in these experiments, natural colonization was sufficient to result in disease suppression and the addition of antagonists had little effect in increasing levels of suppression for both pathogens. On the other hand, in the composted sewage sludge amended medium, natural colonization was found to be sufficient to induce suppression of Rhizoctonia but not Pythium. Addition of the antagonistic microorganisms to this batch of composted sewage sludge in accordance with the invention did successfully induce suppression of Pythium. Furthermore, as noted above, the development of suppressiveness in compost media not amended with antagonistic microorganisms is highly variable and unpredictable. These experiments therefore indicated that adding antagonistic microorganisms to compost after peak heating provides a practicable method of inducing predictable levels of suppressiveness to both Rhizoctonia and Pythium.

Further experiments with composted hardwood bark indicated that the combinations of T. hamatum 382 or 559 in combination with Flavobacterium 299 were effective in inducing suppression not only to Rhizoctonia and Pythium but also to wilt caused by Fusarium oxysporum f. sp. conglutinans race 2.

It will be apparent to those skilled in the art that numerous changes and improvements can be made in the preferred embodiments of the invention described above without departing from the scope of the invention. Accordingly, the foregoing description is to be construed in an illustrative and not in a limitative sense, the scope of the invention being defined solely by the appended claims.

I claim:

1. A biologically pure culture for inducing suppression of plant pathogens and/or diseases caused thereby in a compost, said culture consisting essentially of at least one Trichoderma fungus selected from the group consisting of Trichoderma hamatum isolate 382, A.T.C.C. No. 20765 and T. hamatum isolate 559, A.T.C.C. No. 20764, and at least one bacterium selected from the group consisting of Pseudomonas maltophilia sp. isolate 76, A.T.C.C. No. 53199 and Flavobacterium sp. isolate 299, A.T.C.C. No. 53198.

2. A culture according to claim 1 consisting essentially of a mixture of T. hamatum isolate 382, A.T.C.C. No. 20765 and Flavobacterium sp. isolate 299, A.T.C.C. No. 53198.

3. A culture according to claim 1 consisting essentially of a mixture of T. hamatum isolate 559, A.T.C.C. No 20764 and Flavobacterium sp. isolate 299, A.T.C.C. No. 53198.

4. A method for producing a compost which is suppressive to at least Rhizoctonia solani and Pythium ultimum and/or diseases caused thereby, which method comprises inoculating into said compost at least one Trichoderma fungus selected from the group consisting of Trichoderma hamatum isolate 382, A.T.C.C. No. 20765 and T. hamatum isolate 559, A.T.C.C. No. 20764, and at least one baterium selected from the group consisting of Pseudomonas maltophilia sp. isolate 76, A.T.C.C. No. 53199 and Flavobacterium sp. isolate 299, A.T.C.C. No. 53198.

5. A method according to claim 4 wherein said inoculation is effected after peak heating has been achieved but before substantial recolonization of said compost by mesophilic microoganisms has occurred.

6. A method according to claim 4 wherein the compost is inoculated with *T. hamatum* isolate 382, A.T.C.C. No. 20765 and Flavobaterium sp. isolate 299, A.T.C.C. No. 53198.

7. A method according to claim 4 wherein the compost is inoculated with *T. hamatum* isolate 559, A.T.C.C. No 20764 and Flavobacterium sp. isolate 299, A.T.C.C. No. 53198.

8. A method according to claim 4 wherein said inoculation is effected by adding to the compost a biologically pure culture consisting essentially of said at least one Trichoderma and said at least one baterium.

9. A method according to claim 4 wherein said compost is composted hardwood bark or composted pine bark.

10. A method according to claim 4 wherein said compost is composted sewage sludge.

11. A method according to claim 4 wherein at least about 100 colony forming units of each of said fungus and said baterium are added to each gram dry weight of said compost.

12. A method according to claim 11 wherein from about $10^5$ to about $5 \times 10^7$ cells of each of said fungus and said bacterium are added to each gram dry weight of said compost.

13. A method for producing a compost which is suppressive to a plant pathogen and/or disease caused thereby, which method comprises inoculating into said compost, after peak heating has been achieved but before substantial recolonization of said compost by mesophilic microorganism has occurred, a microorganism culture combination consisting essentially of at least one fungus antagonistic to *Rhizoctonia solani* and suppressive to plant disease caused thereby and at least one bacterium antagonistic to *Pythium ultimum* and suppressive to plant disease caused thereby with innoculating by at least 100 colony forming units each of said fungus and of said bacterium for each gram of the compost, based on dry weight of the compost.

14. A method according to claim 13 wherein said compost is composted hardwood bark or composted pine bark.

15. A method according to claim 13 wherein said compost is composted sewage sludge.

16. A method according to claim 13 wherein there is inoculated into said compost at least one Trichoderma fungus antagonistic to *Rhizoctonia solani* and at least one bacterium antagonistic to *Pythium ultimum*.

17. A method according to claim 16 wherein said fungus and bacterium also render said compost suppressive to disease caused by *Fusarium oxysporum* f. sp. *conglutenans*.

18. A biologically pure culture consisting essentially of any one or more of the following microorganisms:

*Trichoderma hamatum* isolate 382, A.T.C.C. No. 20765;

*Trichoderma hamatum* isolate 559, A.T.C.C. No. 20764;

*Pseudomonas maltophilia* sp. isolate 76, A.T.C.C. No. 53199; and

Flavobacterium sp. isolate 299, A.T.C.C. No. 53198.

* * * * *